United States Patent [19]

Brittain et al.

[11] 4,066,651

[45] Jan. 3, 1978

[54] ALKANOIC ACID 2-QUINOLINE DERIVATIVES

[75] Inventors: David Robert Brittain; Edward Douglas Brown; Walter Hepworth; Gilbert Joseph Stacey, all of Macclesfield, England

[73] Assignee: Imperial Chemical Industries Limited, London, England

[21] Appl. No.: 662,685

[22] Filed: Mar. 1, 1976

[30] Foreign Application Priority Data

Mar. 20, 1975 United Kingdom .............. 11644/75
Oct. 14, 1975 United Kingdom .............. 42043/75

[51] Int. Cl.$^2$ ........................................... C07D 215/22
[52] U.S. Cl. ............................. 260/287 K; 424/258; 260/289 K; 260/576
[58] Field of Search ................................... 260/287 K

[56] References Cited

U.S. PATENT DOCUMENTS 3,772,301  11/1973  Strandtmann .................. 260/287 K

OTHER PUBLICATIONS

Kegasawa et al., "Chemical Abstracts," 1968, vol. 69:106,760n.

Primary Examiner—Donald G. Daus
Assistant Examiner—David E. Wheeler
Attorney, Agent, or Firm—Cushman, Darby & Cushman

[57] ABSTRACT

Novel 1,2-dihydro-2-oxoquinol-4-ylalkanoic acid derivatives bearing a variety of substituents on the quinoline nucleus but including, at position 1, an aromatic radical linked directly or through a $C_{1-4}$-alkylene or a $C_{2-4}$-alkenylene radical. Representative compounds of the invention are 1-(3,4-dichlorobenzyl)-3-methyl-1,2-dihydro-2-oxoquinol-4-ylacetic acid and α-(1-benzyl-1,2-dihydro-2-oxoquinol-4-yl)propionic acid. The compounds possess anti-inflammatory or analgesic properties, or are inhibitors of the enzyme aldose reductase.

5 Claims, No Drawings

ALKANOIC ACID 2-QUINOLINE DERIVATIVES

This invention relates to new quinolone alkanoic acid derivatives and in particular it relates to new quinolone alkanoic acid derivatives which have useful pharmaceutical properties.

According to the invention there is provided a quinolone alkanoic acid derivative of the formula:-

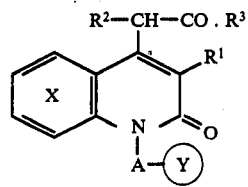

wherein A is a direct bond, or a $C_{1-4}$-alkylene or $C_{2-4}$-alkenylene radical; $R^1$ is hydrogen or a halogen atom or a $C_{1-4}$-alkyl radical; $R^2$ is hydrogen or a $C_{1-4}$-alkyl radical; $R^3$ is a hydroxy, amino, hydroxylamino, $C_{1-6}$-alkoxy or a phenoxy radical which may optionally bear one or two substituents selected from halogen atoms, nitro, trifluoromethyl, $C_{1-4}$-alkyl and $C_{1-4}$-alkoxy radicals; and wherein the benzene ring X may optionally bear 1 or 2 substituents selected from halogen atoms, $C_{1-6}$-alkyl, $C_{1-4}$-alkoxy, $C_{1-4}$-alkylthio, trifluoromethyl, $C_{1-3}$-alkylenedioxy, nitro, amino, $C_{1-4}$-alkylamino, di-($C_{1-4}$-alkyl)-amino and $C_{2-4}$-alkanoylamino radicals and from $C_{7-10}$-aralkoxy radicals optionally substituted by a halogen atom; and wherein the ring Y is a phenyl radical which may optionally bear 1,2 or 3 substituents selected from halogen atoms, $C_{1-6}$-alkyl, $C_{1-4}$-alkoxy, $C_{1-4}$-alkylthio, $C_{1-4}$-alkylsulphinyl, $C_{1-4}$-alkylsulphonyl, $C_{1-4}$-alkylamino, di-($C_{1-4}$-alkyl)amino, nitro, cyano, trifluoromethyl and $C_{2-8}$-alkoxyalkyl radicals and from $C_{6-10}$-aryl radicals optionally substituted by 1 or 2 halogen atoms; or wherein the ring Y is a naphthyl or a monocyclic heterocyclic aromatic radical which may optionally bear 1 or 2 substituents selected from halogen atoms, $C_{1-4}$-alkyl and $C_{1-4}$-alkoxy radicals; or a pharmaceutically acceptable salt thereof.

It will be observed that those compounds of formula I wherein $R^2$ is a $C_{1-4}$-alkyl radical contain an asymmetric carbon atom and that accordingly, such compounds can be isolated in a racemic form and two optically active forms. This specification is addressed to the racemic form of the compounds of formula I wherein $R^2$ is a $C_{1-4}$-alkyl radical and to any optical isomer which shows any one or more of the useful pharmaceutical properties mentioned hereinafter; it being a matter of general knowledge how to resolve the racemic form and to determine the biological properties of the optical isomers.

A particularly suitable value for A when it is a $C_{1-4}$-alkylene radical is, for example, a methylene or ethylene (—$CH_2 \cdot CH_2$—) radical.

A particularly suitable value for A when it is a $C_{1-4}$-alkenylene radical is for example a propenylene (—$CH_2 \cdot CH=CH$—) radical and preferably, a propenylene radical having the unsaturated bond in conjugation with the ring Y.

A particularly suitable value for $R^1$ when it is a halogen atom is for example a fluorine, chlorine or bromine atom, and when it is a $C_{1-4}$-alkyl radical, a particularly suitable value is, for example a methyl or ethyl radical.

A particularly suitable value for $R^2$ when it is a $C_{1-4}$-alkyl radical is, for example, a methyl or ethyl radical.

A particularly suitable value for $R^3$ when it is a $C_{1-6}$-alkoxy radical is for example, a methoxy, ethoxy, n-butoxy or t-butoxy radical.

A particularly suitable value for a $C_{1-4}$-alkyl or $C_{1-4}$-alkoxy radical which may be present on a phenoxy radical when it is a value for $R^3$ is, for example, a methyl or methoxy radical respectively.

A particularly suitable value for a halogen atom which may be present on a phenoxy radical when it is a value for $R^3$ is, for example, a chlorine or bromine atom.

A particularly suitable value for a halogen atom when it is a substituent on ring X or Y is, for example, a fluorine, chlorine, bromine or iodine atom.

A particularly suitable value for a $C_{1-6}$-alkyl radical when it is a substituent on ring X or Y is, for example, a methyl, ethyl, n-propyl, i-propyl, n-butyl or t-butyl radical.

A particularly suitable value for a $C_{1-4}$-alkoxy radical when it is a substituent on ring X or Y is, for example, a methoxy or ethoxy radical.

A particularly suitable value for a $C_{1-4}$-alkylthio radical when it is a substituent on ring X or Y is, for example, a methylthio radical.

A particularly suitable value for a $C_{1-4}$-alkylsulphinyl radical when it is a substituent on ring Y is, for example a methylsulphinyl radical.

A particularly suitable value for a $C_{1-4}$-alkylsulphonyl radical when it is a substituent on ring Y is, for example, a methylsulphonyl radical.

A particularly suitable value for a $C_{1-4}$-alkylamino radical when it is a substituent on ring X or Y is, for example, a methylamino radical.

A particularly suitable value for a di-($C_{1-4}$-alkyl)-amino radical when it is a substituent on ring X or Y is, for example, a dimethylamino radical.

A particularly suitable value for a $C_{1-3}$-alkylenedioxy radical when it is a substituent on ring X is, for example a methylenedioxy, ethylenedioxy or 2,2-propylenedioxy radical.

A particularly suitable value for a $C_{2-4}$-alkanoylamino radical when it is a substituent on ring X is, for example, an acetamido radical.

A particularly suitable value for a $C_{7-10}$-aralkoxy radical when it is a substituent on ring X is, for example, a benzyloxy radical.

A particularly suitable value for a $C_{7-10}$-aralkoxy radical optionally substituted by a halogen atom when that radical is a substituent on ring X is, for example, a chlorobenzyloxy radical, for example a 4-chlorobenzyloxy radical.

A particularly suitable value for a $C_{2-8}$-alkoxyalkyl radical when it is a substituent on ring Y is for example, an n-propoxymethyl radical.

A particularly suitable value for a $C_{6-10}$-aryl radical when it is a substituent on ring Y is for example a phenyl radical.

A particularly suitable value for a $C_{6-10}$-aryl radical optionally substituted by 1 or 2 halogen atoms when that radical is a substituent on ring Y is, for example, a chlorophenyl radical, for example, a 4-chlorophenyl radical.

It is to be understood that throughout this specification the numbering given to substituents in ring X relates to the actual position of attachment to the quinolone nucleus. Thus, for example, a 6-chloro substituent on ring X is to be interpreted as meaning a 6- chloroquinoline derivative. Accordingly, specific particularly suitable arrangements of substituents on ring X are, for example, no substituents, or a 6-chloro, 6-bromo, 6-fluoro, 6-fluoro-7-ethoxy, 7-chloro, 7-fluoro, 6,7-difluoro, 6-methyl, 7-methyl, 6-n-butyl, 6,7-dimethyl, 6-methoxy, 7-methoxy, 8-methoxy, 7-ethoxy, 6,7-methylenedioxy, 6-benzyloxy, 6-(4-chlorobenzyloxy), 6-methylthio, 6-nitro, 6-amino, 6-acetamido, 6-dimethylamino, or a 6-methylamino substituent.

A particularly suitable value for ring Y when it is a naphthyl radical is, for example, a 2-naphthyl radical.

A particularly suitable value for ring Y when it is a monocyclic heterocyclic aromatic radical is for example such a radical having a 5- or 6-membered ring, for example, a furyl, thienyl or a pyridyl radical, for example, a fur-2-yl, thien-2-yl or a pyrid-2-yl radical.

A particularly suitable value for a $C_{1-4}$-alkyl or $C_{1-4}$-alkoxy radical which may be present as a substituent on a monocyclic heterocyclic aromatic radical when the latter radical is a value for ring Y is, for example, a methyl or methoxy radical, respectively.

A particularly suitable value for a halogen atom which may be present as a substituent on a monocyclic heterocyclic aromatic radical when the latter is a value for ring Y is, for example, a fluorine, chlorine or bromine atom.

Specific particularly suitable values for ring Y are, for example, a phenyl, 2-chloro-, 3-chloro-, 4-chloro-, 4-fluoro-, 4-bromo-,4-iodo-, 2,4-dichloro-, 3,4-dichloro-, 3,4-difluoro-, 3,4-dibromo-, 3-chloro-4-bromo-, 4-chloro-2-methyl-, 4-chloro-3-trifluoromethyl-, 4-chloro-2-fluoro-, 2-chloro-4-fluoro-, 4-bromo-3-methyl-, 3,4,5-trichloro-, 3,4,5-tribromo-, 3,5-dichloro-4-bromo-, 2-methyl-, 4-methyl-, 4-ethyl-, 4-i-propyl-, 4-n-propyl-, 4-t-butyl-, 4-n-butyl-, 3,4-dimethyl-, 3,4,5-trimethyl-, 4-methoxy, 4-n-propoxymethoxy-, 4-methylamino-, 4-dimethylamino-, 4-methylthio-, 4-methylsulphinyl-, 4-methylsulphonyl-, 4-nitro-, 4-cyano-, 4-p-chlorophenyl-, 3-trifluoromethyl-, or a 4-trifluoromethyl-phenyl; or a biphenyl, naphth-2-yl, pyrid-2-yl, pyrid-4-yl, 4,6-dimethylpyrid-2-yl, fur-2-yl, 5-methyl-fur-2-yl, 4,5-dibromo-fur-2-yl, thien-2-yl, 4,5-dimethylthien-2-yl or a 4,5-dichlorothien-2-yl radical.

Particularly suitable salts of a compound of formula I which is sufficiently basic, for example, a compound of formula I wherein ring X and/or ring Y bear at least one $C_{1-4}$-alkylamino or di-($C_{1-4}$-alkyl-)amino group or wherein ring Y is a pyridyl radical, are pharmaceutically acceptable acid addition salts derived from an appropriate organic acid or an inorganic acid, for example hydrochloric acid. Particularly suitable salts of a compound of formula I which is sufficiently acidic, for example, a compound of formula I wherein $R^3$ is a hydroxy radical, are pharmaceutically acceptable base-addition salts, for example, alkali metal or alkaline earth metal salts, for example, sodium, potassium, calcium or magnesium salts, aluminium salts, or salts of organic bases affording a pharmaceutically acceptable cation, for example, triethanolamine.

A particularly preferred group of compounds of the invention comprises those compounds formula I wherein $R^3$ is a hydroxy radical.

Specific compounds of formula I are set out in the Examples.

The compounds of the formula I may be made by any process applicable to the manufacture of chemically-analogous compounds. Such processes are exemplified by the following in which A, $R^1$, $R^2$, $R^3$, ring X and ring Y have the meanings stated above unless specifically stated otherwise:- a. For a compound of formula I wherein $R^3$ is a hydroxy radical, hydrolysing and decarboxylating a malonate of the formula:-

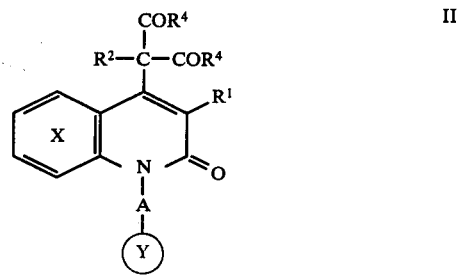

wherein $R^4$ is a $C_{1-4}$-alkoxy radical, or an acid-addition salt thereof.

It is to be understood that in the above reaction the steps of hydrolysis and decarboxylation may be carried out together, for example, in the same vessel, for example, in the presence of acid, or separately for example, by akaline hydrolysis followed by decarboxylation in the presence of acid. Thus the hydrolysis and decarboxylation may be carried out together by reacting the malonate of formula II with an inorganic acid, for example sulphuric acid, in the presence of water at an elevated temperature, for example 50° C. to 150° C., and more particularly 80° C. to 120° C., for example under reflux. Alternatively, the hydrolysis and decarboxylation may be carried out separately by reacting the malonate with an inorganic base, for example an alkali metal hydroxide, for example sodium hydroxide, in the presence of water at an elevated temperature, for example as stated immediately above, and then acidifying the resulting salt of a substituted malonic acid so as to give the substituted malonic acid itself, and then decarboxylating the latter compound. The acidification may be carried out using an inorganic acid, for example sulphuric acid, and the decarboxylation may be carried out by heating the reaction mixture comprising the substituted malonic acid at an elevated temperature, for example as stated above.

The above hydrolysis and decarboxylation may optionally be carried out in the presence of an organic solvent, for example a $C_{1-4}$-alkanol, for example ethanol. In the case where the hydrolysis and decarboxylation is carried out by means of an inorganic acid, the organic solvent may be, for example, acetic acid.

The malonates of formula II which are used as starting materials in the above-mentioned process may be obtained by reacting a compound of the formula:

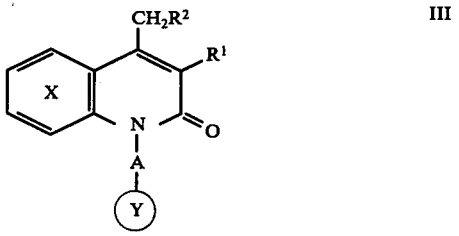

with a carbonate of the formula $R^4COR^4$, wherein $R^4$ has the meaning stated above, and sodium hydride or potassium hydride. The reaction may be carried out in an excess of the carbonate reactant, and/or it may be carried out in dimethylformamide. The reaction is conveniently carried out under reflux. The compounds of the formula III themselves can be obtained in an analogous manner to known processes for preparing 4-methyl-1-phenylcarbostyril and 1-benzyl-4-methylcarbostyril. It is to be noted that in a few cases a substituent in the ring X can be so reactive as to react with the carbonate reactant $R^4COR^4$, or a decomposition product thereof, that displacement of the radical occurs so that the corresponding alkoxy derivative is obtained. This happens, for example, in the case of at least some 7-fluoro derivatives (see Examples 30 and 38), but the corresponding 7-fluoro end-products can be obtained by alternative procedures (see Examples 86 and 87).

In the case of compounds of formula III wherein $R^2$ is hydrogen, reaction as described hereinbefore with sodium hydride or potassium hydride and a carbonate of the formula $R^4COR^4$, results in the intermediate formation of a sodium or potassium salt respectively of the corresponding malonate of formula II wherein $R^2$ is hydrogen. This sodium or potassium salt may either be acidified to yield the corresponding malonate of formula II wherein $R^2$ is hydrogen or, more conveniently, may be reacted with a $C_{1-4}$-alkyl halide, for example a $C_{1-4}$-alkyl bromide or iodide, to give the corresponding malonate of formula II wherein $R^2$ is a $C_{1-4}$-alkyl radical. The alkylation may be carried out in a suitable non-aqueous organic solvent, for example, dimethylformamide, and may conveniently be carried out at from 20° C. to 160° C., for example, under reflux.

b. For a compound of formula I wherein $R^3$ is a hydroxy radical, hydrolysing and decarboxylating a pyruvic acid derivative of the formula:

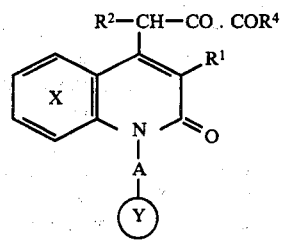

wherein $R^4$ is a $C_{1-4}$-alkoxy radical as stated above

The hydrolysis and decarboxylation may be carried out be reacting the pyruvic acid derivative of formula IV with a strong inorganic acid, for example, concentrated sulphuric acid or polyphosphoric acid, at an elevated temperture, for example at 50° C. to 100° C. Alternatively, it may be carried out by hydrolysing the pyruvic acid derivative of formula IV using aqueous inorganic acid or using base, for example, aqueous hydrochloric acid or sodium or potassium hydroxide, to obtain the corresponding pyruvic acid, followed by decarboxylation of this by reaction thereof wth hydrogen peroxide in aqueous alkali metal hydroxide, for example, sodium hydroxide. The above mentioned hydrolysis is optionally carried out under the influence of heat, for example, at from 20° C. to 100° C., and conveniently in the presence of a $C_{1-4}$-alkanol, for example, ethanol. The above mentioned reaction with hydrogen peroxide is conveniently carried out, for example, in water at a temperature, for example, of from $-10°$ C. to 30° C., preferably, at 0° C.

The pyruvic acid derivative of formula IV which are used as starting materials in the above process may be obtained by reacting a compound of formula III with an oxalate of the formula $(R^4CO)_2$ wherein $R^4$ is a $C_{1-4}$-alkoxy radical, with sodium or potassium or a hydride, amide or $C_{1-4}$-alkoxide thereof, at 0° C. to 100° C. The reaction may be carried out in an excess of the oxalate reactant, and/or in the presence of an inert organic solvent, for example ether, benzene, tetrahydrofuran or dimethylformamide. The compounds of the formula III themselves may be obtained in an analogous manner to known processes for preparing 4-methyl-1-phenylcarbostyril and 1-benzyl-4-methylcarbostyril.

c. Reacting an alkali derivative of the formula:

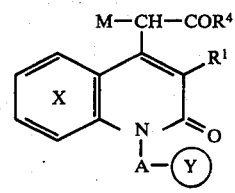

wherein $R^4$ is a $C_{1-4}$-alkoxy radical, and M is an alkali metal atom, with a $C_{1-4}$-alkyl halide.

A particularly suitable alkali metal atom is, for example a sodium or potassium atom. The starting material of formula V is conveniently obtained in situ by reacting the appropriate compound in which M is replaced by a hydrogen atom, that is a compound of formula I wherein $R^2$ is hydrogen and $R^3$ is a $C_{1-4}$-alkoxy radical, with for example, sodium or potassium or a hydride, amide or $C_{1-4}$-alkoxide thereof. A particularly suitable $C_{1-4}$-alkyl halide is for example a $C_{1-4}$-alkyl iodide or bromide, for example, methyl iodide or ethyl bromide. The reaction may be carried out in an inert organic solvent for example dimethylformamide and at a temperature of, for example, 20° C. to 160° C.

d. For a compound of formula I wherein the benzene ring X bears at least one nitro group, nitrating the corresponding compound of formula I wherein the benzene ring X is either unsubstituted or bear 1–2 substituent(s) which are not nitro groups.

The nitration may be carried out by any standard method for the nitration of a benzene ring which is fused to a heterocyclic ring, for example by reacting the starting material with concentrated sulphuric acid and an alkali metal nitrate, for example, potassium nitrate, at about 0° C.

e. For a compound of formula I wherein the benzene ring X bears at least one amino radical, reducing the nitro group(s) in the corresponding compound of formula I wherein the benzene ring X bears at least one nitro group.

The reduction may be carried out by any known suitable procedure, for example by reducing the nitro compound with iron powder in 50% v/v aqueous acetic acid at about 90° C.

f. For a compound of formula I wherein $R^3$ is a hydroxy radical, reacting an alkali metal derivative of the formula:

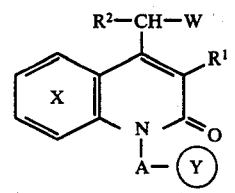

wherein W is a lithium, sodium or potassium atom, with dry carbon dioxide in a suitable dry organic solvent at approximately $-30°$ C. to about $-50°$ C. and in an inert atmosphere, and then treating the product thereby obtained with water at ambient temperature approximately.

A particularly suitable organic solvent is an ether, for example tetrahydrofuran or diethyl ether, and a particularly suitable inert atmosphere is provided, for example, by the use of dry argon. The treatment of the intermediate product with water is preferably carried out at approximately pH 3–4, and at 10° C. to 25° C.

The starting materials of the formula VI may be obtained in a conventional manner, for example by reacting a compound of formula III with a metalating agent, for example n-butyl lithium. n-Butyl-lithium, is preferably used in the presence of triethylamine (which activates the n-butyl-lithium) in a suitable dry ether, for example tetrahydrofuran or diethyl ether, at approximately −30° C. to −50° C. and in an inert atmosphere, for example an atmosphere composed of dry argon. Alternatively the metalating agent may be, for example, phenyl-lithium, phenyl-sodium or potassium hydride.

g. Reacting a compound of the formula:

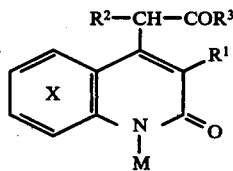

VII wherein M is an alkali metal atom, with a compound of the formula:

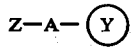

VIII wherein A is a $C_{1-4}$-alkylene or $C_{2-4}$-alkenylene radical and Z is a bromine or iodine atom when A is a methylene radical, an iodine atom when A is an $C_{2-4}$-alkylene radical, and a bromine or iodine atom when A is a $C_{2-4}$-alkenylene radical.

The reaction of a compound of formula VII with that of formula VIII is conveniently carried out in the presence of a suitable organic solvent, for example, hexamethylphosphoramide, and at a temperature of for example from 10° C. to 100° C., conveniently at ambient temperature.

The starting materials of formula VII are conveniently obtained in situ by reacting the appropriate compound in which M is replaced by a hydrogen atom, that is a 1,2-dihydro-2-oxoquinoline derivative, with, for example, sodium hydroxide or potassium hydroxide at, for example, ambient temperature. The appropriate 1,2-dihydro-2-oxoquinoline starting materials are themselves obtained by reacting an alkali metal derivative of the formula:

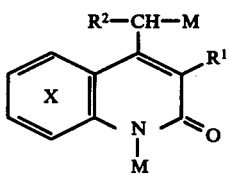

IX wherein M is an alkali metal atom, with carbon dioxide using similar reaction conditions to those specified in connection with part (f) of the process above.

h. For a compound of formula I wherein $R^3$ is an amino, hydroxylamino, $C_{1-4}$-alkoxy or a phenoxy radical which may optionally bear one or two substituents selected from halogen atoms, nitro, trifluoromethyl, $C_{1-4}$-alkyl and $C_{1-4}$-alkoxy radicals, condensing a quinolone alkanoic acid of the formula:

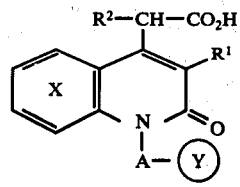

X that is a compound of formula I wherein $R^3$ is a hydroxy radical, or a reactive derivative thereof, with an active hydrogen compound of the formula HQ wherein Q is an amino, hydroxylamino, $C_{1-4}$-alkoxy or a phenoxy radical which may optionally bear one or two substituents selected from halogen atoms, nitro, trifluoromethyl, $C_{1-4}$-alkyl and $C_{1-4}$-alkoxy radicals.

A particularly suitable reactive derivative of a compound of formula X is, for example, an acid halide, for example an acid chloride or acid bromide, an acid azide, an acid anhydride or a mixed acid anhydride derived from the acid of formula X. When a reactive derivative is used the reaction is preferably carried out in the presence of base, for example pyridine or triethylamine and conveniently, in an inert solvent or diluent, for example, chloroform, methylene chloride, 1,2-dimethoxyethane or tetrahydrofuran, and at a temperature of, for example, from 0° C. to 100° C.

Alternatively the condensation may be carried out in the presence of a condensing agent for example dicyclohexylcarbodiimide or a mixture of diethylazodicarboxylate and triphenylphosphine. When dicyclohexylcarbodiimide is used, the reaction is preferably carried out in an inert diluent or solvent, for example chloroform, methylene chloride, 1,2-dimethoxyethane or tetrahydrofuran, and conveniently at a temperature of, for example, from 10° C. to 100° C; when a mixture of diethylazodicarboxylate and triphenylphosphine is used, the reaction is preferably carried out in an inert diluent or solvent, for example diethyl ether, and at a temperature of, for example, from 0° C. to 80° C. and, preferably, at 18° C. to 25° C.

The reactive derivative of a compound of formula X may in addition be a $C_{1-4}$-alkyl or phenyl ester thereof when the active hydrogen compound of the formula HQ is hydroxylamine or ammonia. In this particular case the condensation reaction is conveniently carried out in a suitable solvent, for example a $C_{1-4}$-alkanol, for example ethanol or methanol, and at a temperature of from 15° C. to 100° C., and it is preferable to use an excess of the hydroxylamine or ammonia reagent.

i. For a compound of formula I wherein $R^3$ is a hydroxy radical, oxidising a compound of the formula:

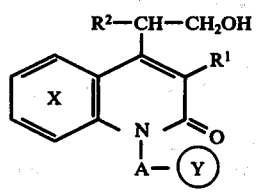

XI

The oxidation is conveniently carried out using for example, an inorganic oxidising agent, for example, potassium permanganate or chromium trioxide, and is preferably carried out in the presence of a mineral acid, for example sulphuric acid. The oxidation is conveniently performed in a polar organic solvent or diluent, for example acetone, and at a temperature of, for example, from 0° C. to 100° C. and conveniently at from 20° C. to 25° C.

The starting materials of formula XI are obtained from the corresponding alkali metal derivative of the formula IX, for example the lithium derivative, with chloromethyl benzyl ether in a mixture of hexamethylphosphoramide and tetrahydrofuran at approximately −20° C., to give the corresponding intermediate of the formula:

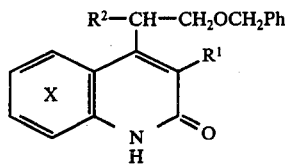

The intermediates of formula XII are then metalated and reacted with the appropriate halide of formula VIII using analogous conditions to those described for the reaction of a compound of formula VII with that of formula VII in part (g) of the above process, to give an intermediate of the formula:

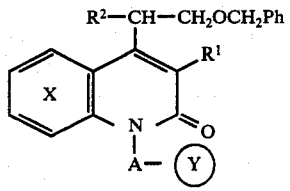

The intermediates of formula XIII are then debenzylated using standard conditions, for example hydrogenation over palladium-charcoal catalyst, to give the required starting materials of formula XI.

j. For a compound of formula I wherein $R^3$ is a hydroxy radical, hydrolysing a compound of the formula:

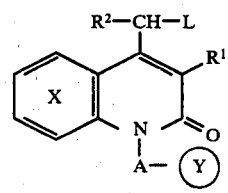

wherein L is a cyano radical or a radical of the formula $CO.R^5$ wherein $R^5$ is a $C_{1-6}$-alkoxy, aryloxy, aralkoxy or amino radical. A particularly suitable value for $R^5$ when it is a $C_{1-6}$-alkoxy radical is, for example, a n-butoxy, ethoxy or methoxy radical and, when it is an aryloxy or aralkoxy radical, is, for example, a phenoxy, p-chlorophenoxy or a benzyloxy radical.

The hydrolysis is preferably carried out under basic or acidic conditions. Particularly suitable basic conditions are provided by an alkali metal hydroxide, for example, sodium or potassium hydroxide. Particularly suitable acidic conditions are provided by a mineral acid, for example, hydrochloric or sulphuric acid. The hydrolysis is carried out in the presence of water, and an organic solvent, for example acetic acid or a $C_{1-4}$-alkanol, for example ethanol, may also be present. The reaction is conveniently carried out at, for example, 40° C. to 150° C., for example at reflux temperature.

Those of the starting materials of formula XIV wherein L is a cyano radical may be obtained from the corresponding pyruvic ester of formula IV by the following sequence of reactions using standard conditions for the preparation of analagous compounds:

i. formation of the pyruvic ester oxime by reaction with hydroxylamine hydrochloride in a mixture of ethanol and pyridine under reflux;

ii. basic hydrolysis of the pyruvic ester oxime to the pyruvic acid oxime followed by decarboxylation and dehydration to the required nitrile of formula XIV.

The above processes can be operated so that a quinoline alkanoic acid of formula I may be isolated as such, or as a pharmaceutically acceptable salt thereof. Such a pharmaceutically acceptable salt may be obtained by conventional procedures when the compound of formula I is sufficiently acidic or basic as hereinbefore defined.

Depending on its chemical structure a compound of the invention possesses analgesic or anti-inflammatory properties, or possesses the property of inhibiting the enzyme aldose reductase. It is to be understood that any particular compound of the invention may possess one or more, but not necessarily all, of the above properties. In addition, some of the compounds of the invention possess the property of inhibiting the enzyme prostaglandin synthetase.

In general, particularly good analgesic properties and/or good anti-inflammatory properties are possessed by those compounds of formula I wherein $R^2$ is a $C_{1-4}$-alkyl radical, of which those wherein $R^2$ is a methyl radical are preferred; good inhibition of the enzyme aldose reductase is in general shown by those compounds of formula I wherein $R^2$ is hydrogen.

Compounds which possess analgesic and/or anti-inflammatory properties have been used in the clinical treatment of the pain and/or inflammation associated with inflammatory diseases, for example rheumatoid or osteoarthritis or ankylosing spondylitis.

Those compounds of the invention which are inhibitors of aldose reductase are useful in the reduction or prevention of the development of the peripheral effects of diabetes, for example the effects of macular oedema, cataract, retinopathy or impaired neural conduction.

Particularly preferred compounds of the invention are:

a. as inhibitors of aldose reductase:
1-(3,4-dichlorobenzyl)-6-fluoro-1,2-dihydro-2-oxoquinol-4-ylacetic acid, 1-(4-bromobenzyl)-6-fluoro-1,2-dihydro-2-oxoquinol-4-ylacetic acic, 1-(3,4-dichlorobenzyl)-1,2-dihydro-2-oxoquinol-4-ylacetic acid, 6-fluoro-1-(4-iodobenzyl)-1,2-dihydro-2-oxoquinol-4-ylacetic acid, 1-(3,4-dichlorobenzyl)-3-methyl-1,2-dihydro-2-oxoquinol-4-ylacetic acid, 1-(4-bromo-3-chlorobenzyl)-6-fluoro-1,2-dihydro-2-oxoquinol-4-ylacetic acid, 1-(3,4-dibromobenzyl)-6-fluoro-1,2-dihydro-2-oxoquinol-4-ylacetic acid, 1-(3,4-dichlorobenzyl)-6-fluoro-3-methyl-1,2-dihydro-2-oxoquinol-4-ylacetic acid, 1-(3,4-dichlorobenzyl)-6,7-difluoro-1,2-dihydro-2-oxoquinol-4-ylacetic acid, 1-(3-chloro-4-bromobenzyl)-3-methyl-1,2-dihydro-2-oxoquinol-4-ylacetic acid; and 1-(3,5-dichloro-4-bromobenzyl)-3-methyl-1,2-dihydro-2-oxoquinol-4-ylacetic acid b. as anti-inflammatory agents:

α-[1-(4-chlorobenzyl)-6-methyl-1,2-dihydro-2-oxoquinol-4-yl]propionic acid, and α(1-benzyl-6-methyl-1,2-dihydro-2-oxoquinol-4-yl)propionic acid;

c. as analgesic agents:

α-(1-benzyl-1,2-dihydro-2-oxoquinol-4-yl)propionic acid, α[1-(4-methylbenzyl)-1,2-dihydro-2-oxoquinol-4-yl]-propionic acid, α-(1-benzyl-6-methyl-1,2-dihydro-2-oxoquinol-4-yl)propionic acid, α[1-(4-methylbenzyl)-6-methyl-1,2-dihydro-2-oxoquinol-4-yl]propionic acid, α-[1-(4-chlorobenzyl)-6-methyl-1,2-dihydro-2-oxoquinol-4-yl]propionic acid, α[1-(4-ethylbenzyl)-1,2-dihydro-2-oxoquinol-4-yl]propionic acid, α-[1-(4-trifluoromethylbenzyl)-1,2-dihydro-2-oxoquinol-4-yl]propionic acid, α-(1-benzyl-7-methyl-1,2-dihydro-2-oxoquinol-4-yl)-propionic acid, and α-[1-(-4-trifluoromethylbenzyl)-6-methyl-1,2-dihydro-2-oxoquinol-4-yl]propionic acid;

d. as inhibitors of prostaglandin synthetase:

α-[1-(4-methylbenzyl)-6-methyl-1,2-dihydro-2-oxoquinol-4-yl]propionic acid and α-[1-(4-methylbenzyl-1,2-dihydro-2-oxoquinol-4-yl]propionic acid; and pharmaceutically acceptable salts thereof.

The biological properties of any particular compound of the invention may be demonstrated by their behaviour in the following standard tests:

a. Aldose reductase inhibition

Inhibition of the enzyme aldose reductase may be demonstrated either in vitro or in vivo.

Thus, in the in vitro test, purified aldose reductase is isolated in known manner from bovine lenses. The percentage inhibition of this enzyme's ability in vitro to reduce aldoses to polyhydric alcohols, and particularly to reduce glucose to sorbitol, caused by a test compound is then determined using standard spectrophotometric methods.

In the in vivo test, rats are made diabetic by dosing with streptozotocin and are then dosed daily with the test compound for 4 days. The animals are then killed and the eye lenses and sciatic nerves are removed. After a standard work-up procedure the residual sorbitol levels in each tissue are determined by gas liquid chromatography after conversion to the poly trimethylsilyl derivatives. Inhibition of aldose reductase in vivo is then assessed by comparing the residual sorbitol levels in tissues from the dosed diabetic group of rats with those of an undosed group of diabetic rats and an undosed, normal group of rats. Active compounds in this test reduce the residual sorbitol levels to levels which are similar to those of normal, undosed rats.

b. Anti-inflammatory activity

This activity is demonstrated in either of the standard tests of adjuvant induced arthritis or carrageenin induced oedema, both of which tests are in rats.

c. Analgesic activity

This activity is demonstrated in a standard analgesic test which involves the induction of writhing in mice following intraperitoneal injection of acetylcholine.

d. Prostaglandin Synthetase Inhibition

This activity is demonstrated in a standard in vitro test, which involves the use of prostaglandin synthetase isolated from the ram.

The potency of any particular compound depends upon its chemical structure, but in general, depending upon the particular test involved, an active compound is active at a dose or molar concentration in the range:

a. (aldose reductase inhibition-in vitro test): $10^{-8}$ to $10^{-5}$M; (aldose reductase inhibition-in vivo test): 10–200 mg./kg.;

b. (anti-inflammatory activity — adjuvant arthritis test): 1 – 100 mg./kg.; (anti-inflammatory activity — carrageenin oedema test): 5 – 200 mg./kg.

c. (analgesic activity): 1–200 mg./kg.;

d. (inhibition of prostaglandin synthetase): $10^{-6}$ to $10^{-4}$M.

The particularly preferred compounds mentioned hereinbefore show activity in one or more of the above tests at a minimum dose or molar concentration in the range:

a. (aldose reductase inhibition — in vitro test): $10^{-8}$ to $10^{-7}$M.; (aldose reductase inhibition — in vivo test): 10–100 mg./kg.

b. (anti-inflammatory activity — adjuvant arthritis test): 1–50mg./kg. (anti-inflammatory activity — carrageenin oedema test): 5–50mg./kg.

c. (analgesic activity) — 1–25 mg./kg.;

d. (prostaglandin synthetase inhibition): $10^{-6}$ to $10^{-5}$M.

No overt toxic or other undesirable effects have been detected with the compounds of the invention at doses at which activity is detected in one or more of the above-mentioned tests.

When a compound of the invention is used to produce an effect in warm-blooded animals, it may be administered orally at the following daily doses:

a. to inhibit the enzyme aldose reductase: a daily dose of 5 to 100mg./kg.; in man this is equivalent to a total daily dose of 50 to 1200mg. per 70kg. man;

b. to obtain an anti-inflammatory effect: a daily dose of 5 to 150 mg./kg.; in man this is equivalent to a total daily dose of 50 to 1500mg. per 70kg. man.

c. to obtain an analgesic effect: a daily dose of 5 to 150mg./kg.; in man this is equivalent to a total daily dose of 50 to 1500mg. per 70kg. man; the daily doses may conveniently be given in divided form.

When 1-(3,4-dichlorobenzyl)-3-methyl-1,2-dihydro-2-oxoquinol-4-ylacetic acid is used to obtain an effect in warm-blooded animals as mentioned in (a) immediately above, a daily oral dose of 20 to 50 mg./kg. is administered; in man this is equivalent to a total daily dose of 200 to 600mg. per 70kg. man.

When α-(1-benzyl-1,2-dihydro-2-oxoquinol-4-yl)-propionic acid is used to obtain an effect in warm-blooded animals as mentioned in (b) and/or (c) immediately above, a daily oral dose of 5 to 20mg./kg. is administered; in man this equivalent to a total daily dose of 50 to 250mg. per 70kg. man.

The compounds of the invention may be administered in the form of pharmaceutical compositions and according to a further feature of the invention there is provided a pharmaceutical composition which comprises a compound of formula I or a pharmaceutically acceptable salt thereof in pharmaceutically acceptable form.

By "pharmaceutically acceptable form" is meant either a pharmaceutical preparation in which the compound is associated with a pharmaceutically acceptable diluent or carrier, or a pharmaceutical preparation, for example a capsule, in which the compound is confined in a unit dosage form without necessarily being associated with a diluent or carrier.

Especially preferred pharmaceutically acceptable forms are those suitable for oral administration, for example tablets, capsules, suspensions or solutions, which may be obtained by conventional methods and, if desired, may incorporate conventional diluents, carriers or other excipients. Other preferred pharmaceutically acceptable forms are those suitable for parenteral administration, for example sterile injectable aqueous or non-aqueous solutions or suspensions, and for rectal administration, for example suppositories. Dosage forms should contain from 50mg. to 500mg. of a compound of formula I per dosage unit.

Compositions intended for use in the treatment of the peripheral effects of diabetes, may also contain other agents whch may have a beneficial effect on the disease or on associated conditions, for example a known hypoglycaemic agent, for example tolbutamide.

Compositions intended for use in the treatment of the pain and/or the inflammation of inflammatory diseases may also contain other known agents having analgesic and/or anti-inflammatory properties, for example paracetamol, codeine, acetyl salicylic acid, chloroquine, phenylbutazone, D-penicillamine, indomethacin, ibuprofen, naproxen, ketoprofen, or an anti-inflammatory steroid, for example prednisolone, or a uricosuric agent, for example probenecid.

The invention is illustrated, but not limited by the following Examples:

EXAMPLE 1

A solution of 1-(4-chlorobenzyl)-1,2-dihydro-4-methyl-2-oxoquinoline (18.0g.) in diethyl carbonate (80ml.) was added to a stirred suspension of sodium hydride (15.4g.; weighed as a 60% w/w dispersion in oil, but subsequently washed by decantation with light petroleum, b.p. 40°-60° C., to remove the oil) in diethyl carbonate (20ml.). The mixture was stirred unfer reflux for 1½ hours, and formed a thick suspension. This was cooled and treated with a small amount of methanol to destroy any remaining sodium hydride. Dilution with ether (400 ml.) gave a suspension from which the solid was filtered. This was suspended in ethanol (180ml.) and brought to pH 3 by addition of hydrochloric acid. Water (600ml.) was added, and the suspension was stirred for 30 minutes before the solid was collected by filtration, washed with water, and well drained. This solid [which comprised diethyl 1-(4-chlorobenzyl)-1,2-dihydro-2-oxoquinol-4-ylmalonate] was dissolved in ethanol (180ml.), to which was added aqueous 40% w/v sodium hydroxide (20ml.), and the mixture was heated under reflux for 4 hours. The cooled mixture was added to water (600ml.) to give a solution which was brought to pH 3 by addition of concentrated hydrochloric acid. The resultant precipitate was collected by filtration, washed with water, drained, and crystallised from ethanol to give 1-(4-chlorobenzyl)-1,2-dihydro-2-oxoquinol-4-ylacetic acid, m.p. 208°-209° C, in 51% overall yield.

By an analogous procedure, but starting from the appropriately sustituted 1,2-dihydro-4-methyl-2-oxoquinolines, the following compounds were prepared in 15-65% yield.

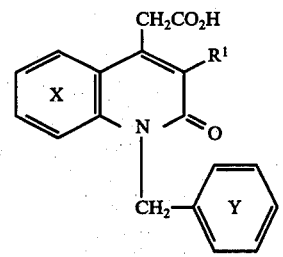

XV

| Example | Substituent(s) on ring X | Substituent(s) on ring Y | Recrystallisation solvent | M.p. (° C.) (decomposition) |
|---|---|---|---|---|
| 2 | — | — | EtOH | 194-5 |
| 3 | — | 4-OMe | MeOH | 182-3 |
| 4 | 6-Cl | — | EtOH | 221-2 |
| 5 | 6-Cl | 4-OMe | Pr$^n$OH | 188-9 |
| 6 | 6-OMe | — | EtOH | 196-7 |
| 7 | 6-OMe | 4-Cl | * | 205-6 |
| 8 | 6-OMe | 4-OMe | EtOH | 191-2 |
| 9 | — | 2,4-Cl$_2$ | MeOH | 202-3 |
| 10 | — | 3-CF$_3$ | EtOH | 203 |
| 11 | — | 4-isoPr | MeOH | 186-7 |
| 12 | 6,7-OCH$_2$O | 3,4-Cl$_2$ | dimethyl formamide ("DMF") | 213 |
| 13 | 6,7-OCH$_2$O | 4-Cl | DMF-H$_2$O (3/1 v/v) | 208 |
| 14 | 6-Br | 4-Cl | DMF-H$_2$O (3/1 v/v) | 207 |
| 15 | — | 4-Cl, 3-CF$_3$ | * | 203 |
| 16 | — | 2-Me, 4-Cl | * | 207 |
| 17 | 6-n-Bu | 4-Cl | MeOH | 199 |
| 18 | 6-F | 4-Cl | MeOH | 205 |
| 19 | — | 2-Cl | MeOH | 201-3 |
| 20 | 6-OMe | 2-Cl | DMF-MeOH (1/1 v/v) | 219 |
| 21 | — | 4-F | MeOH | 193 |
| 22 | 8-OMe | 4-Cl | EtOH | 192-3 |
| 23 | 7-OMe | 4-Cl | * | 203 |
| 24 | 6-Me | 4-Cl | DMF | 330 |
| 25 | — | 3-Cl | * | 182-5 |
| 26 | — | 4-Br | * | 193 |
| 27 | 6-p-Clbenzyloxy | 4-Cl | DMF-H$_2$O (3/1 v/v) | 185 |
| 28 | 6F | 4-n-Pr | MeOH-H$_2$O (4/1 v/v) | 176-7 |
| 29 | — | 4-n-PrOCH$_2$ | MeOH | 178-9 |
| 30 | 6-F-7-OEt$^1$ | 3,4-Cl$_2$ | MeCN | 188 |
| 31 | 6-F | 4-Br | isoPrOH-H$_2$O (4/1 v/v) | 194-6 |
| 32 | 6-F | 4-Me | * | 195 |
| 33 | — | 4-Me$_2$N | EtOH | 197 |
| 34 | 6-MeCONH | 4-Cl | * | 210 |
| 35 | — | 4-Me | EtOH | 193 |
| 36 | 6-MeS | 3,4-Cl$_2$ | DMF-H$_2$O (3/1 v/v) | 209 |
| 37 | 6-F | — | MeOH | 189-90 |
| 38 | 7-OEt$^2$ | 3,4-Cl$_2$ | MeCO$_2$H | 195-6 |

-continued

| Example | Substituent(s) on ring X | Substituent(s) on ring Y | Recrystallisation solvent | M.p. (° C.) (decomposition) |
|---|---|---|---|---|
| 39 | 6-F | 4-I | MeOH | 193–4 |
| 40 | 7-Me | 3,4-Cl$_2$ | * | 209 |
| 41 | 6-F | 3-Cl, 4-Br | CH$_3$CN | 189–91 |
| 42 | 6-F | 3,4-Br$_2$ | MeOH-H$_2$O (4/1 v/v) | 188 |
| 43 | — | 2-F, 4-Cl | MeOH | 199 |
| 44 | — | 2-Cl, 4-F | * | 196–7 |
| 45 | 6,7-OCMe$_2$O | 3,4-Cl$_2$ | EtOH | 227 |
| 46 | 6-Cl | 4-Cl | * | 192 |
| 47 | 7-Cl | 3,4-Cl$_2$ | EtOH | 222–3 |
| 48 | 6-F | 4-F | EtOH | 188 |
| 49 | 6-F | 4-t-Bu | EtOAc-cyclohexane (1/1 v/v) | 182 |
| 50 | 6-F | 3,4,5-Me$_3$ | * | 187–8 |
| 51 | 6-F | 4-CN | * | 196 |
| 52 | 6-F | 3-Me, 4-Br | EtOH | 197 |
| 53 | 6-F | 3,4-F$_2$ | EtOH | 189–90 |
| 54 | 6,7-O(CH$_2$)$_2$O | — | DMF-MeOH (1/1 v/v) | 199 |
| 55 | —$^3$ | 3,4-Cl$_2$ | MeOH | 217–8 |

*Purified by dissolution in 2N-aqueous ammonia and reprecipitation with 2N-hydrochloric acid.
$^1$This compound was obtained from the corresponding 6,7-difluoro compound, i.e. under the described reaction conditions the 7-fluoro substituent was replaced by a 7-ethoxy substituent. End products containing a 7-fluoro substituent can be obtained by alternative processes, see Examples 86 and 87.
$^2$Essentially as with the compound mentioned in footnote 1, this compound was obtained from the corresponding 7-fluoro compound.
$^3$This compound also contained a methyl substituent at the 3-position of the quinolone nucleus.

The N-aralkylquinoline derivatives used as starting materials in these preparations were usually obtained by forming the anions of the parent quinolines with sodium hydride in dimethylformamide, and then treating them with the appropriate aralkyl chlorides at temperatures up to 100° C. Complications arising from O-aralkylation were sometimes encountered, but these could be avoided by first preparing the N-aralkylanilines and converting these into the quinolines by known procedures. These procedures are described in Example 74.

The following new intermediates were prepared by such methods:

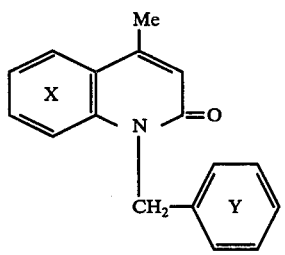

XVI

| Substituent on ring X | Substituent(s) on ring Y | Recrystallisation solvent | M.p: (° C.) |
|---|---|---|---|
| — | 4-Cl | MeOH | 126–7 |
| — | 4-OMe | MeOH/H$_2$O (washed with light petroleum) | 160–2 |
| 6-Cl | — | | 102–4 |
| 6-Cl | 4-Cl | MeOH | 165–8 |
| 6-Cl | 4-OMe | C$_6$H$_6$/C$_6$H$_{12}$ | 157.5–9 |
| 6-OMe | — | C$_6$H$_{12}$ | 117–8 |
| 6-OMe | 4-Cl | C$_6$H$_6$/C$_6$H$_{12}$ | 170–2 |
| 6-OMe | 4-OMe | MeOH | 155–6 |
| — | 2-Cl | C$_6$H$_{12}$ | 165–7 |
| 6-OMe | 2-Cl | MeOH | 177–9 |
| — | 3,4-Cl$_2$ | MeOH | 130–1 |
| — | 3-CF$_3$ | EtOH | 146–7 |
| — | 3-IsoPr | petroleum ether b.p. 60–80° C. | 88–90 |
| 6,7-OCH$_2$O | 3,4-Cl$_2$ | MeOH | 199–202 |
| 6,7-OCH$_2$O | 4-Cl | MeOH | 197–200 |
| 6-Br | 4-Cl | EtOH | — |
| — | 4-Cl-3-CF$_3$ | MeOH | 165–7 |
| — | 2-Me-4-Cl | EtOH | 197–9 |
| 6-n-Bu | 4-Cl | MeOH | 113–4 |
| 6-F | 4-Cl | MeOH | 154–6 |
| — | 2-Cl | MeOH | 180–3 |
| 6-OMe | 2-Cl | MeOH | 177–9 |

-continued

| Substituent on ring X | Substituent(s) on ring Y | Recrystallisation solvent | M.p: (° C.) |
|---|---|---|---|
| — | 4-F | MeOH-H$_2$O (4/1 v/v) | 193 |
| 8-OMe | 4-Cl | MeOH | 104 |
| 7-OMe | 4-Cl | EtOH | 193–5 |
| 6-Me | 4-Cl | MeOH | 156–8 |
| — | 3-Cl | EtOH | 115–6 |
| — | 4-Br | EtOH | 137–9 |
| 6-F | 4-Et | petroleum ether b.p. 60–80° C. | 114–6 |
| 6-F | 4-n-Pr | petroleum ether b.p. 60–80° C. | 110–2 |
| 6-F | 4-Br | cyclohexane | 153–4 |
| 6-F | — | cyclohexane | 144–6 |
| 7-F | 3,4-Cl$_2$ | cyclohexane | 175–7 |
| 6-F | 3,4-Br$_2$ | toluene | 180–1 |
| 6-F | 3,4,5-Br$_3$ | DMF-MeOH (1/1 v/v) | 217–9 |
| 6-F | 3-Cl, 4-Br | toluene | 170–2 |
| 6-F | 4-t-Bu | petroleum ether b.p. 60–80° C. | 78 |
| 6-F | 4-Me | EtOH | 140–1 |
| 6-F | 3,4-Me$_2$ | petroleum ether b.p. 60–80° C. | 128–30 |
| — | 4-Me | petroleum ether b.p. 80–100° C. | 93–4 |
| 6-F | 4-I | cyclohexane | 161 |
| 7-Cl | 3,4-Cl$_2$ | petroleum ether b.p. 60–80° C. | 166–7 |
| 7-Me | 3,4-Cl$_2$ | MeOH | 175–6 |
| 6-F | 3-Me, 4-Br | cyclohexane | 151 |
| 6-F | 3,4-F$_2$ | EtOH | 150–2 |
| 6-F | 4-CN | toluene | 158–60 |
| 6,7-F$_2$ | 3,4-Cl$_2$ | EtOAc | 206–8 |
| 6-F | 3,4,5-Me$_3$ | EtOH | 135–6 |
| 6-p-Cl-benzyloxy | 4-Cl | chloroform | 169–70 |
| —* | 3,4-Cl$_2$ | petroleum ether b.p. 80–100° C. | 128 |

*This compound contained a methyl substituent at the 3-position of the quinolone nucleus.

EXAMPLE 56

Diethyl 1,2-dihydro-2-oxo-1-phenylquinol-4-ylmalonate (2.7g.) was dissolved in ethanol (50 ml.), and a solution of sodium hydroxide (2.85 g.) in water (3 ml.) was added. The mixture was heated under reflux for 1 hour, and then cooled and poured into water (200 ml.) to give a solution which was treated with decolourising carbon, filtered, and adjusted to pH 3 by addition of hydrochloric acid. The precipitate was collected by filtration, washed with water, drained, and crystallised from methanol to give 1,2-dihydro-2-oxo-1-phenyl-quinol-4-ylacetic acid, m.p. 185.5°–186° C. (decomposition), in 51% yield.

The malonate used as starting material was obtained as follows:

A mixture of 1,2-dihydro-4-methyl-2-oxo-1-phenyl-quinoline (4.7 g.), sodium hydride (4.8 g., 60% w/w dispersion in oil, washed as in Example 1) and diethyl carbonate (50 ml.) was stirred under reflux for 2 hours. Any excess of sodium hydride was then destroyed by addition of methanol to the cooled suspension, and the mixture was then poured into ether (1 l.). The yellow precipitate was collected by filtration, and washed with ether (200 ml.). It was suspended in ethanol (50 ml.), concentrated hydrochloric acid was added to give a pH of 3, and the resultant solution was poured into water (200 ml.). The precipitate was extracted into ether, and the combined extracts were washed with water, dried over magnesium sulphate, and evaporated in vacuo. A sample of the residual solid was recrystallised from a mixture of benzene and cyclohexane to give diethyl 1,2-dihydro-2-oxo-1-phenylquinol-4-ylmalonate, m.p. 101°–103° C.

EXAMPLE 57

6-Chloro-1-(4-chlorobenzyl)-1,2-dihydro-4-methyl-2-oxoquinoline (7.9 g.) was added to a suspension of sodium hydride (6.0 g., 60% w/w dispersion in oil, washed as in Example 1) in diethyl carbonate (100 ml.). The mixture was then stirred and heated under reflux for 3 hours. A small quantity of methanol was added to the cooled suspension to destroy any remaining sodium hydride, and the mixture was then poured into ether (1 l.) to give a solid which was collected and washed well with ether. This solid (16 g.) was suspended in dimethylformamide (40 ml.), and methyl iodide (30.0 g.) was added. The mixture was stirred at room temperature for 1 hour and then heated under reflux on the steam-bath for 1 hour. The mixture was cooled and poured into water (200 ml.) to give an oil which was extracted into ethyl acetate, washed three times with water, and, after drying over magnesium sulphate, was recovered by evaporation under reduced pressure. The residual oil (4.8 g.), which comprised diethyl α-[6-chloro-1-(4-chlorobenzyl)-1,2-dihydro-2-oxoquinol-4-yl]-α-methylmalonate, was dissolved in a mixture of ethanol (50 ml.) and aqueous 40% w/v sodium hydroxide (4ml.), and heated under reflux for 2 hours. The resultant suspension was poured into water (200ml.) to give a solution which was adjusted to pH 3 by addition of concentrated hydrochloric acid. The precipitate was collected by filtration, washed with water, drained well, and recrystallised from aqueous ethanol togive α-[6-chloro-1-(4-chlorobenzyl)-1,2-dihydro-2-oxoquinol-4-yl]propionic acid, m.p. 192.5°–193.5° C, (decomposition) in 43% yield.

In analogous manner, but starting from the appropriately substituted 1-benzyl-1,2-dihydro-4-methyl-2-oxoquinolines and using the requisite alkyl iodides, the following compounds were prepared in yields of 30–62%.

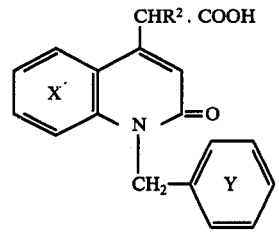

XVII

| Example | Substituent on ring X | Substituent(s) on ring Y | R² | Recrystallisation solvent | M.p. (° C.) (decomposition) |
|---|---|---|---|---|---|
| 58 | — | — | Me | * | 179–180 |
| 59 | — | 4-Cl | Me | MeCN | 186–6.5 |
| 60 | — | 4-OMe | Me | C₆H₆ | 166.7 |
| 61 | 6-Cl | 4-OMe | Me | AcOH/H₂O (4/1 v/v) | 203.5–4 |
| 62 | 6-OMe | 4-Cl | Me | MeCN | 185–6 |
| 63 | — | 2-Cl | Me | EtOH | 201–2 |
| 64 | — | — | Et | MeCN | 194–4.5 |
| 65 | 6-OMe | 2-Cl | Me | MeOH | 187–8 |
| 66 | 6-Cl | — | Me | Toluene-cyclohexane (1/1 v/v) | 172–3 |
| 67 | 6-OMe | — | Me | EtOH | 179–80 |
| 68 | 6-OMe | 4-OMe | Me | * | 182–3 |
| 69 | — | 2,4-Cl₂ | Me | MeOH | 187–9 |
| 70 | — | 4-F | Me | MeOH | 193 |
| 71 | 6,7-OCH₂O | 4-Cl | Me | EtOH | 199–200 |
| 72 | 6-F | 3,4-Cl₂ | Me | DMF-MeOH (1/1 v/v) | 195–6 |

*Purified by dissolution in 2N-aqueous ammonia and reprecipitation with 2N-hydrochloric acid The required appropriately substituted 1-benzyl-1,2-dihydro-4-methyl-2-oxo-quinolines are described in Examples 1 – 55. The following additional starting materials were obtained in a similar manner to that described for the starting materials in Example 1 – 55:

1-(2,4-dichlorobenzyl)-1,2-dihydro-4-methyl-2-oxoquinoline, m.p. 137°–8° C.;

1-(3,4-dichlorobenzyl)-1,2-dihydro-6-fluoro-4-methyl-2-oxoquinoline, m.p. 182°–3° C.

EXAMPLE 73

Ethyl 1-(4-chlorobenzyl)-1,2-dihydro-2-oxoquinol-4-ylpyruvate (25g.) was dissolved in concentrated sulphuric acid (100ml.) and heated at 80° C. until a test sample no longer gave a positive colour reaction with aqueous ferric chloride solution (2 to 3 hours). The mixture was then cooled, poured into ice-water (1 l.), the resulting mixture filtered, and the solid residue washed with water, drained and crystallised from ethanol to give 1-(4-chlorobenzyl)-1,2-dihydro-2-oxoquinol-4-ylacetic acid, m.p. 208°–209° C, in 48% yield.

The starting material was obtained as follows:

Sodium hydride (18g.; 60% w/w dispersion in oil, washed as described in Example 1) was stirred in dry dimethylformamide (300 ml.), and 1-(4-chlorobenzyl)-1,2-dihydro-4-methyl-2-oxoquinoline (64.7g.) was added, followed by diethyl oxalate (55 g.). The mixture was stirred at room temperature for 2.5 hours with occasional external cooling to keep the temperature below 25° C. Ether (2 l.) was added, and the mixture was filtered. The solid residue was washed with ether (500 ml.), and then suspended in dimethylformamide (200ml.) nd acidified to pH 2 by the addition of concentrated hydrochloric acid. The resultant mixture was added to water (3 l.), and the mixture filtered, and the solid residue washed with water (2 l.), drained well, and crystallised from ethanol to give ethyl 1-(4-chlorobenzyl)-1,2-dihydro-2-oxoquinol-4-ylpyruvate, m.p. 180°–182° C.

EXAMPLE 74

A mixture of 1-o-chlorobenzyl-4-methyl-6-methoxy-2-oxo-1,2-dihydroquinoline (2.5g.), oil-free sodium hydride (obtained from 2.5g. of a 50% w/w suspension as described in Example 1) and diethyl carbonate (50 ml.) was heated over 1 hour to reflux and the reflux maintained for 3 hours. The mixture was cooled and treated with methanol (2ml.) to destroy excess sodium hydride. Ether (200ml.) was added and the yellow precipitate was filtered off, washed with ether (50ml.), and dried, and was then suspended in dimethylformamide (100 ml.) containing methyl iodide (4 ml.). After 24 hours standing at room temperature, the mixture was diluted with water (200 ml.) and the aqueous mixture extracted with ether (3 × 100ml.). The combined ethereal extracts were washed with water (2 × 100ml.), and dried with magnesium sulphate, and the ether was evaporated. The residue, which comprised diethyl α-(1-o-chlorobenzyl-6-methoxy-2-oxo-1,2-dihydroquinol-4-yl)-α-methylmalonate, was dissolved in a solution of potassium hydroxide (3.6 g.) in water (4ml.) and ethanol (100ml.). The mixture was refluxed for 1 hour, cooled, and diluted with N-hydrochloric acid (100ml.). The resulting mixture was filtered, and the solid residue washed with water and crystallised from methanol (100ml.) to give α-(1-o-chlorobenzyl-6-methoxy-2-oxo-1,2-dihydroquinol-4-yl)propionic acid, m.p. 187°–188° C. in 48% yield.

The o-chlorobenzyl derivative used as starting material was obtained as follows:

A solution of 2-chlorobenzaldehyde (70 g.) and 4-methoxyaniline (61.5g.) in toluene (750 ml.) was refluxed under a Dean and Stark separator until no more water collected (ca. 1 hour). The toluene was evaporated in vacuo, and the residue was dissolved in methanol (1.5 l.). The methanolic solution was treated at room temperature with sodium borohydride (60 g.) added portionwise so that, with gentle cooling, the temperature was maintained at 40°–50° C. The solution was then refluxed for 15 minutes, diluted with water (1.5 l.), and the aqueous mixture extracted with ether (3 × 200ml.). The combined ethereal extracts were washed with water (2 × 100 ml.), dried ($K_2CO_3$), and evaporated to give N-(4-methoxyphenyl)-2-chlorobenzylamine as a brown oil, Infra Red $\nu$ max 3400, 1618 cm.$^{-1}$, which was used directly in the next stage.

The above-mentioned benzylamine derivative (42.6 g.) was dissolved in glacial acetic acid (400 ml.) containing mercuric acetate (5.5 g.), and to the solution was added diketen (17.4g.) at room temperature. The mixture was stirred and warmed to 40° C. and, when the exotherm had subsided, the mixture was heated at 70° C. for 15 minutes. The mixture was then cooled and diluted with water (700 ml.), and the aqueous mixture was extracted with ether (1 × 300 ml., 2 × 200 ml.). The combined ethereal extracts were successively washed with saturated aqueous sodium bicarbonate and water, and then dried ($K_2CO_3$) and evaporated to give a brown oil, $\nu$ max 1710, 1650 cm.$^{-1}$. The oil was added dropwise to stirred concentrated sulphuric acid (100ml.) at 70° C. The stirred mixture was kept at 20° C. for 10 minutes after the addition was complete, and then poured into ice-water (500g.). The aqueous mixture was extracted with chloroform (1 × 500 ml., 2 × 200 ml.) and the combined chloroform extracts were washed with water, dried ($MgSO_4$) and evaporated. The residue was crystallised from methanol (120 ml.) to give 1-o-chlorobenzyl-4-methyl-6-methoxy-2-oxo-1,2-dihydroquinoline, m.p. 177°–179° C.

EXAMPLE 75

In similar manner to that described in Example 74, 1-p-chlorophenyl-6-methoxy-4-methyl-2-oxo-1,2-dihydroquinoline gave α-(1-p-chlorophenyl-6-methoxy-2-oxo-1,2-dihydroquinol-4-yl)propionic acid, m.p. 177°–178° C., in 50% yield.

The p-chlorophenyl derivative used as starting material was obtained as follows:

A solution of 4-methoxyacetanilide (30 g.) and 1-chloro-4-iodobenzene (69g.) in nitrobenzene (250ml.) containing potassium carbonate (14 g.) and copper bronze (0.8 g.) was refluxed for 32 hours. The nitrobenzene was removed by steam distillation and the steam-involatile residue was extracted into ether (3 × 200 ml.). The ethereal solution was washed with water, dried ($MgSO_4$) and evaporated. A solution of the residue (36.2 g.) in 2N-ethanolic potassium hydroxide solution (250ml.) was refluxed overnight, and then cooled and diluted with water (1200 ml.). The aqueous mixture was extracted with chloroform (2 × 250 ml.) and the combined extracts were washed with water (2 × 250 ml.), dried ($MgSO_4$) and evaporated to give a dark red solid (26.6 g.) which, on crystallisation from petroleum ether (b.p. 40°–60° C.), gave 4-chloro-4'-methoxydiphenylamine (10 g.), m.p. 52°–53° C. A solution of the residue (from the evaporated mother liquors) in a mixture of ether (25% v/v) and petroleum ether (b.p. 40°–60° C.) was passed down a silica gel column (250 g.), and from the eluate a further quantity of product was obtained.

Mercuric sulphate (43.2g.) was added to a solution of 4-chloro-4'-methoxydiphenylamine (17 g.) in glacial acetic acid (250 ml.) at ambient temperature. Diketen (2 ml.) was added to the stirred mixture and the mixture was warmed (to ca. 40° C.) to initiate the reaction. Diketen (10 ml.) was added dropwise so as to maintain a temperature of 40°–50° C. The mixture was then stirred at room temperature for 1 hour, and then poured into water (1.2 l.). The aqueous mixture was extracted with ether (3 × 200 ml.) and the combined extracts were washed with saturated, aqueous sodium bicarbonate solution. The acid-free ethereal extract was washed with water (2 × 200 ml.), dried ($MgSO_4$) and evaporated to give N-acetoacetyl-4-chloro-4'-methoxydiphenylamine as a red oil, $\nu$ max 1665, 1720 cm.$^{-1}$, which was used directly in the next stage.

The above-mentioned acetoacetyl derivative (12g.) was added portionwise to stirred concentrated sulphuric acid (12 ml.) at room temperature. The mixture was slowly warmed and then kept at 60° C. for 3 hours. The mixture was cooled and poured into water (500 ml.), and the aqueous mixture was extracted with chloroform (3 × 100 ml.). The combined extracts were washed with water (100 ml.), dried (MgSO₄), and evaporated to give an orange oil which crystallized on treatment with ethanol to give, on filtration, 1-p-chlorophenyl-4-methyl-6-methoxy-2-oxo-1,2-dihydroquinoline, m.p. 234°–235° C.

EXAMPLE 76

1-(4-Chlorobenzyl)-1,2-dihydro-2-oxoquinol-4-ylacetic acid (33 g.) was added to concentrated sulphuric acid (210 ml.) at 0° C. The mixture was stirred at 0° C. and potassium nitrate (11g.) was added in small portions over 8 minutes. The mixture was then stirred at 0° C. for a further 10 minutes and then for 2 hours at room temperature. The mixture was poured into an ice-water mixture (2.5 l.), and the precipitated solid was filtered off. The dried solid was crystallised from 3/1 v/v dimethylformamide-ethanol to give 1-(4-chlorobenzyl)-1,2-dihydro-6-nitro-2-oxoquinol-4-ylacetic acid, m.p. 217°–9° C., in 85% yield.

EXAMPLE 77

Iron powder (18g.) was added over 40 minutes to a stirred solution of 1-(4-chlorobenzyl)-1,2-dihydro-6-nitro-2-oxoquinol-4-ylacetic acid (13g.) in 50% v/v aqueous acetic acid (200 ml.) at 90° C. When the addition was completed, the mixture was stirred a further 70 minutes at 90° C. and then poured into an ice-water mixture (700 ml.). The mixture was adjusted to pH 1 with hydrochloric acid, and then filtered. The filtrate was adjusted to pH 6 with ammonium hydroxide solution, and the resulting mixture filtered. The solid residue (13g.) was dissolved as far as possible in 2N-sodium hydroxide solution, and the mixture was filtered. The filtrate was adjusted to pH 6 with glacial acetic acid, and the precipitated solid was filtered off, stirred with hot water (85° C., 200 ml.) and filtered while hot to give 6-amino-1-(4-chlorobenzyl)-1,2-dihydro-2-oxoquinol-4-ylacetic acid, m.p. 196°–9° C., (decomposition) in 52% yield.

EXAMPLES 78–85

The process described in Example 1 was repeated, but using the appropriate 1-benzyl-1,2-dihydro-4-methyl-2-oxoquinoline derivative as starting material, and there were thus obtained the following compounds of formula XV in yields of 25–60%:

| Ex. | Substituent on ring X | Substituent(s) on ring Y | Recrystallisation solvent | M.p. (° C.) (decomposition) |
|---|---|---|---|---|
| 78 | 6-F | 3,4-Cl₂ | MeOH | 196–7 |
| 79 | — | 4-Et | * | 182–3 |
| 80 | 6-F | 4-Et | MeOH | 197–8 |
| 81 | 6-Br | 3,4-Cl₂ | EtOH | 197 |
| 82 | — | 2-Me | * | 207 |
| 83 | — | 4-NO₂ | * | 208–210 |
| 84 | — | 4-n-Bu | MeOH | 174–5 |
| 85 | — | 4-p-ClPh | * | 182–4 |

*Purification by dissolution in 2-N aqueous ammonia and reprecipitation with 2-N hydrochloric acid.

The starting materials of formula XVI used in preparing the above compounds were obtained as described hereinbefore and had the following melting points:

| Substituent on ring X | Substituent(s) on ring Y | Recrystallisation solvent | M.p. (° C.) |
|---|---|---|---|
| 6-F | 3,4-Cl₂ | MeOH | 182–3 |
| — | 4-Et | * | 76–7 |
| 6-F | 4-Et | MeOH | 114–6 |
| 6-Br | 3,4-Cl₂ | washed with EtOH | 183–5 |
| — | 2-Me | washed with EtOH | 172–4 |
| — | 4-NO₂ | EtOH | 149–150 |
| — | 4-n-Bu | * | 58–60 |
| — | 4-p-ClPh | EtOH | 156–8 |

*Purified by chromatography on a column of silica gel; elution with diethyl ether.

EXAMPLE 86

1-(3,4-Dichlorobenzyl)-1,2-dihydro-7-fluoro-4-methyl-2-oxoquinoline (7g.) was added portionwise to a solution of n-butyl-lithium (9.8 ml. of a 2.32 N-solution in hexane) and triethylamine (1.15 g.) in dry tetrahydrofuran (150 ml.) maintained at −40° C. The mixture was stirred at −30° C. to −40° C. for one hour under an atmosphere of dry argon, and then added to a saturated solution of dry carbon dioxide in dry tetrahydrofuran (200 ml.). The mixture was stirred at −30° C. for 2 hours and then allowed to reach ambient temperature overnight. Water (400 ml.) was added and the concentrated hydrochloric acid to bring the pH of the mixture to 3–4. The crude acid was filtered off and recrystallised from methanol to give 1-(3,4-dichlorobenzyl)-1,2-dihydro-7-fluoro-2-oxoquinol-4-ylacetic acid, m.p. 205°–207° C. (dec.), in 66% yield.

EXAMPLE 87

A solution of 1-(3,4-dichlorobenzyl)-6,7-difluoro-1,2-dihydro-4-methyl-2-oxoquinoline (5 g.) in benzene (15 ml.) was added with stirring at ambient temperature to a mixture of diethyl oxalate (2.3 g.), benzene (2 ml.) and a 6N-solution of potassium ethoxide in ethanol (6 ml.). The mixture was allowed to stand overnight at ambient temperature under dry nitrogen. The yellow solid was filtered off, washed with benzene (5 ml.) and dried by suction on the filter. The dried solid (5.7 g.) was mixed with 2.77 N-aqueous sodium hydroxide (21 ml.) at 0° C. and kept at 0° C. overnight. Ice (11.5 g.) and then 100 vol. hydrogen peroxide (4.04 ml.) were added to the mixture and it was again kept overnight at 0° C. A further quantity of 100 vol. hydrogen peroxide (1.7 ml.) was added and the mixture kept at 0° C. for 72 hours. The mixture was then treated with manganese dioxide (1 g.). When the effervescence had ceased the mixture was warmed to 50° C. and filtered. The filter cake was washed with warm 2.77 N-aqueous sodium hydroxide (20 ml.) and the total filtrate acidified with concentrated hydrochloric acid. The precipitate was collected and recrystallised first from a mixture (½ v/v) of ethyl acetate and cyclohexane, and then from ethanol to give 1-(3,4-dichlorobenzyl)-6,7-difluoro-1,2-dihydro-2-oxoquinol-4-ylacetic acid m.p. 185°–7° C. (dec.), in 10% yield.

EXAMPLE 88

α-(1,2-Dihydro-2-oxoquinol-4-yl)propionic acid (217 mg.) was dissolved in a mixture of hexamethylphosphoramide (2 ml.) and 2N-sodium hydroxide (2 ml.). A solution of benzyl bromide (0.528 ml.) in hexamethylphosphoramide (2 ml.) was added dropwise to the stirred solution during 2 hours. The mixture was then poured into water (10 ml.), and the resulting mixture washed with chloroform (3 × 5 ml.). The aqueous solution was acidified to pH 1 with concentrated hydrochloric acid, and the resulting mixture was filtered and the white solid residue washed with water and dried in vacuo over phosphorus pentoxide. The solid was crystallised from ethanol to give α-(1-benzyl-1,2-dihydro-2-oxoquinol-4-yl)propionic acid, m.p. 178°-180° C. (decomposition), in 39% yield.

The propionic acid derivative used as starting material was obtained as follows:

1,2-Dihydro-4-methyl-2-oxoquinoline (79.5 g.) was dissolved in a mixture of dry hexamethylphosphoramide (530 ml.) and tetrahydrofuran (530 ml.), and the solution was cooled to −10° C. under a nitrogen atmosphere. n-Butyl-lithium (1.54 M solution in hexane; 770 ml.) was added to the stirred solution at such a rate as to keep the temperature below 0° C. When the addition was completed, the deep red solution was cooled to −50° C. and methyl iodide (50 ml.) was rapidly added. The resulting pale yellow solution was immediately poured into water (2000 ml.) and acidified to pH 1 with concentrated hydrochloric acid. The resulting mixture was filtered and the solid residue washed with water and then dried in vacuo over phosphorus pentoxide. Crystallisation from ethanol gave 4-ethyl-1,2-dihydro-2-oxoquinoline, m.p. 197° C.

4-Ethyl-1,2-dihydro-2-oxoquinoline (50 g.) was dissolved in a mixture of dry hexamethylphosphoramide (280 ml.) and dry tetrahydrofuran (280 ml.), and the solution cooled to −10° C. under a nitrogen atmosphere. n-Butyl-lithium (1.54 M solution in hexane; 435 ml.) was added at such a rate as to keep the temperature below 0° C. The resulting deep red solution was added to a stirred saturated solution of carbon dioxide in tetrahydrofuran (750 ml.) at −70° C. and under a nitrogen atmosphere. The resulting pale yellow suspension was poured into water (800 ml.), and the mixture was washed with chloroform (3 × 300 ml.). The aqueous solution was acidified to pH 1 with concentrated hydrochloric acid, the resulting mixture filtered, and the solid residue washed with water and dried in vacuo over phosphorus pentoxide. There was thus obtained α-(1,2-dihydro-2-oxoquinol-4-yl)propionic acid, m.p. 196°-8° C. (decomposition).

EXAMPLES 89-91

In a similar manner to that described in Example 88 the following compounds were obtained from the appropriate starting materials, in yields of 32-68%:

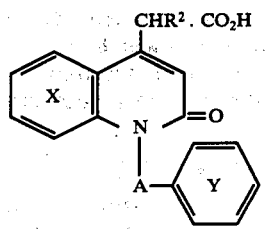

XVIII

| Example | Substituent on ring X | Substituent on ring Y | r² | A | Recrystallisation solvent | m.p. (° C.) |
|---|---|---|---|---|---|---|
| 89 | — | — | H | CH₂ | EtOH | 194-5 |
| 90 | — | — | Me | —CH₂CH=CH—* (trans) | EtOH | 170 |
| 91 | — | 4-Me | Me | CH₂ | Et₂O (precipitated) | 172 |

*note: the ring Y is attached to the double bond.

The starting materials were obtained in analogous manner to that described in Example 88.

EXAMPLE 92

A mixture of α(1-benzyl-1,2-dihydro-2-oxoquinol-4-yl)propionic acid (0.5g.), methanol (5ml.) and concentrated sulphuric acid (4 drops) was heated under reflux for six hours. The mixture was then poured into water (10 ml.), and the resulting mixture was neutralised with sodium bicarbonate solution. The mixture was extracted with ethyl acetate (3 × 5 ml.) and the combined extracts were washed successively with sodium bicarbonate solution (5 ml.) and water (5 ml.), and then dried with sodium sulphate. The solvent was evaporated in vacuo and the residue crystallised from cyclohexane to give methyl α-(1-benzyl-1,2-dihydro-2-oxoquinol-4-yl)propionate m.p. 90°-92.5° C, in 74% yield.

EXAMPLES 93-97

The following compounds of formula X (wherein R¹ is hydrogen) were prepared in a similar manner to that described in Example 57 from the appropriate starting materials, in yields of 30-62%.

| Example | Substituent on ring X | Substituent on ring Y | R² | A | Recrystallisation solvent | m.p. (° C.) |
|---|---|---|---|---|---|---|
| 93 | 6-Me | 4-Cl | Me | CH₂ | EtOH | 206 |
| 94 | 6-Me | 4-F | Me | CH₂ | EtOH | 192 |
| 95 | 6-Me | — | Me | CH₂ | EtOH | 186-7 |
| 96 | — | — | Me | CH₂CH₂ | Water | 176-8 |
| 97 | 6-Me | 4-Me | Me | CH₂ | Ethanol | 194 |

The required starting materials of formula III (wherein R¹ and R² are hydrogen) were obtained in analogous manner to that described in Example 1, and had the following melting points:

| A | Substituent on ring X | Substituent on phenyl ring Y | m.p. ° C. |
|---|---|---|---|
| CH₂ | 6-Me | 4-Cl | 156-158 |
| CH₂ | 6-Me | 4-F | 165-6 |
| CH₂ | 6-Me | — | 141-2 |
| CH₂CH₂ | — | — | 122-4 |
| CH₂ | 6-Me | 4-Me | 134-6 |

EXAMPLES 98-105

The following compounds were prepared in a similar manner to that described in Example 1 from the appropriate starting materials, in yields of 11-57%.

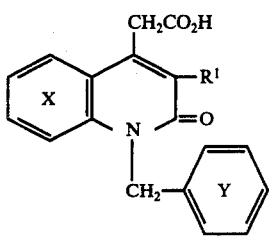

XIX

| Ex. | Substituent on ring X | Substituent on ring Y | $R^1$ | Recrystallisation solvent | (m.p.) (° C.) (decomposition) |
|---|---|---|---|---|---|
| 98 | 6-Me | — | H | EtOH | 201 |
| 99 | 6-F | 3,4-$Cl_2$ | Me | MeOH | 219-222 |
| 100 | — | 3,4-$Cl_2$ | Et | MeOH | 231-2 |
| 101 | — | 3,4-$Cl_2$ | Cl | MeOH | 197-8 |
| 102 | 6-F | 4-$CF_3$ | H | EtOH | 285 |
| 103 | 6,7-$Me_2$ | 3,4-$Cl_2$ | H | dimethylformamide/MeOH, 1:1 v/v | 197 |
| 104 | 6,7-$F_2$ | 3,4-$Cl_2$ | H | EtOAc/cyclohexane, 1:1 v/v | 182-5 |
| 105 | 6-F | 3,4,5-$Cl_3$ | H | MeOH | 280-2 |

The corresponding 1-benzyl-1,2-dihydro-4-methyl-2-oxo-quinoline starting materials of the formula:

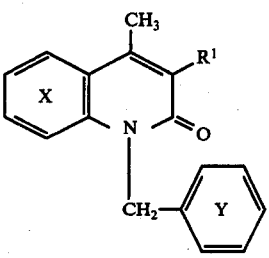

XX were obtained by an analogous method to that described in Example 1 and had the following melting points:

| $R^1$ | Substituent on ring X | Substituent on ring Y | m.p. ° C. |
|---|---|---|---|
| H | 6-Me | — | 141-2 |
| Me | 6-F | 3,4-$Cl_2$ | 148-50 |
| Et | — | 3,4-$Cl_2$ | 116-8 |
| Cl | — | 3,4-$Cl_2$ | 128-9 |
| H | 6-F | 4-$CF_3$ | 154-5 |
| H | 6,7-$Me_2$ | 3,4-$Cl_2$ | 182-3 |
| H | 6,7-$F_2$ | 3,4-$Cl_2$ | 206-8 |
| H | 6-F | 3,4,5-$Cl_3$ | 208-9 |

EXAMPLE 106-107

The following compounds were prepared in a similar manner to that described in Example 1 from the appropriate starting materials:

6-fluoro-1-(naphth-2-ylmethyl)-1,2-dihydro-2-oxoquinol-3-ylacetic acid, m.p. 195° C., (19% yield) crystallised from toluene (Example 106); and 1-(pyrid-2-ylmethyl)-1,2-dihydro-2-oxoquinol-4-ylacetic acid hydrochloride, m.p. 210°-2° C., (15% yield) after washing with ethanol (Example 107).

The starting materials were obtained by an analogous method to that described in Example 1, and had the following melting points:

6-fluoro-1-(naphth-2-ylmethyl)-4-methyl-1,2-dihydro-2-oxo-quinoline, m.p. 146°-7° C.

1-(pyrid-2-ylmethyl)-4-methyl-1,2-dihydro-2-oxo-quinoline, m.p. 129°-30° C.

EXAMPLE 108

Using an analogous procedure to that described in Example 86, 3-methyl-1-(naphth-2-ylmethyl)-1,2-dihydro-2-oxo-quinol-4-ylacetic acid, m.p. 186° C. (recrystallised from ethanol) was obtained in 18% yield from 3,4-dimethyl-1-(naphth-2-ylmethyl)-1,2-dihydro-2-oxo-quinolone, m.p. 124°-5° C.

EXAMPLE 109

A stirred solution of 4-(2-hydroxyethyl)-6-fluoro-1-(3,4,5-tribromobenzyl)-1,2-dihydro-2-oxoquinoline (1.8g.) in acetone (700 ml.) at 25° C. was treated with Jones reagent ($CrO_3$ (267g.) in concentrated sulphuric acid (23 ml.) diluted with water to 100 ml. 2.5 ml.). After 30 minutes, isopropanol (0.5ml.) was added to the mixture which was then filtered through kieselguhr. The filtrate was diluted to 1.8 l. with water. Acetone was then distilled out until the solution was faintly hazy. The cooled solution yielded crystals on cooling which were filtered off and recrystallised from ethyl acetate. There was thus obtained 6-fluoro-1-(3,4,5-tribromobenzyl)-1,2-dihydro-2-oxoquinol-4-ylacetic acid, m.p. 207° C. (decomposition), in 71% yield.

The required starting material, 4-(2-hydroxyethyl)-6-fluoro-(3,4,5-tribromobenzyl)-1,2-dihydro-2-oxoquinoline, was obtained as follows:

6-Fluoro-4-methyl-1,2-dihydro-2-oxoquinoline (10g.) was suspended in a mixture of dry hexamethylphosphoramide (68ml.) and dry tetrahydrofuran (68ml.) and the suspension was cooled to −20° C. under an argon atmosphere. n-Butyllithium (1.6M. solution in n-hexane; 78ml.) was added at such a rate that the temperature was maintained below 0° C. To the resulting deep red solution, there was added at −20° C. chloromethyl benzyl ether (8.5g.), as rapidly as possible. The mixture was stirred at −20° C. for one hour and then diluted with water (200ml.). The mixture was partially evaporated in vacuo to remove the tetrahydrofuran and then extracted with ethyl acetate (3 × 150ml.). The combined organic extracts were washed with water (2 × 100ml.), dried ($MgSO_4$) and evaporated. The residue was recrystallised from isopropanol and there was thus obtained 4-(2-benzyloxyethyl)-6-fluoro-1,2-dihydro-2-oxo-quinoline, m.p. 135°-140° C.

To a suspension of sodium hydride (0.675g. of 80% w/w suspension; freed of mineral oil as in Example 1) in dimethylformamide (100ml.) under a nitrogen atmosphere was added 4-(2-benzyloxyethyl)-6-fluoro-1,2-dihydro-2-oxoquinoline (6.0g.). The mixture was stirred at 40° C. for one hour and then treated at this temperature with 3,4,5-tribromobenzylbromide (9.1g.). The mixture was stirred overnight at ambient temperature and then diluted with water (200 ml.) and the product extracted with ethyl acetate (3 × 150ml.). The combined organic extracts were washed with water (2 × 100ml.), dried ($MgSO_4$), and evaporated. The residue was a mixture of O- and N-substituted products. Chromatography of this residue on silica gel using a 50:50 v/v mixture of ether and petroleum ether (b.p. 40°–60° C.) as eluant gave 4-(2-benzyloxyethyl)-6-fluoro-1-(3,4,5-tribromobenzyl)-1,2-dihydro-2-oxoquinoline, as an oil, Infra-Red Spectral Absorption $\nu$ max. 1665 cm.$^{-1}$.

A solution of 4-(2-benzyloxyethyl)-6-fluoro-1-(3,4,5-tribromobenzyl)-1,2-dihydro-2-oxoquinoline (6.0g.) in a mixture of dioxan (50ml.), ethanol (50ml.), and concentrated hydrochloric acid (2ml.) was hydrogenated at atmospheric pressure over 5% palladium on carbon (1g.). The theoretical quantity of hydrogen (390ml. at N.T.P.) was absorbed in four minutes. The hydrogenation was stopped and the mixture filtered. Evaporation of the filtrate gave the crude product which was recrystallised twice from methanol to give 4-(2-hydroxyethyl)-6-fluoro-1-(3,4,5-tribromobenzyl)-1,2-dihydro-2-oxoquinoline, m.p. 199°–201° C., in 71% yield.

EXAMPLES 110–111

In a similar manner to that described in Example 109 there was obtained, from 4-(2-hydroxyethyl)-3-methyl-1-(3-chloro-4-bromobenzyl)-1,2-dihydro-2-oxoquinoline, m.p. 142°–143° C., 3-methl-1-(3-chloro-4-bromobenzyl)-1,2-dihydro-2-oxoquinol-4-ylacetic acid (Example 110), m.p. 219°–221° C. (decomposition) recrystallised from ethyl acetate in 73% yield, and from 4-(2-hydroxyethyl)-3-methyl-(3,5-dichloro-4-bromobenzyl)-1,2-dihydro-2-oxoquinoline, m.p. 132°–135° C., 3-methyl-1-(3,5-dichloro-4-bromobenzyl)-1,2-dihydro-2-oxoquinol-4-ylacetic acid (Example 111), m.p. 250°–252° C. (decomposition) (recrystallised from 2-ethoxyethanol), in 60% field.

The following new intermediates necessary for the preparation of Example 110 and Example 111 were obtained using similar procedures to those described in Example 109 and had the following characteristic properties:

4-(2-benzyloxyethyl)-3-methyl-1,2-dihydro-2-oxoquinoline, m.p. 157°–160° C.; 4-(2-benzyloxyethyl)-3-methyl-1-(3-chloro-4-bromobenzyl)-1,2-dihydro-2-oxoquinoline, oil, Infra-red Spectral Absorption, $\nu$ max. 1660 cm.$^{-1}$; 4-(2-benzyloxyethyl)-3-methyl-1-(3,5-dichloro-4-bromobenzyl)-1,2-dihydro-2-oxoquinoline, 143°–4° C.

EXAMPLE 112

In a similar manner to that described in Example 109 there was obtained in 51% yield, 6-fluoro-1(3,4-dichlorobenzyl)-1,2-dihydro-2-oxoquinol-4-ylacetic acid, m.p. 198°–199° C. (decomposition), from 4-(2-hydroxyethyl)-6-fluoro-1-(3,4-dichlorobenzyl)-1,2-dihydro-2-oxoquinoline, m.p. 191°–2° C., which starting material was itself obtained in a similar manner to that described in Example 109 from 4-(2-benzyloxyethyl)-6-fluoro-1-(3,4-dichlorobenzyl)-1,2-dihydro-2-oxoquinoline, m.p. 122°–4° C.

EXAMPLES 113–115

In a similar manner to that described in Example 88 there were obtained in yields of 32–68% the following compounds of formula XVII but from the corresponding starting $\alpha$-(1,2-dihydro-2-oxoquinol-4-yl)propionic acid and the appropriate benzyl halide:

| Example | R$^2$ | Substituent on ring X | Substituent on ring Y | Recrystallisation Solvent | m.p. ° C. (decomposition) |
|---|---|---|---|---|---|
| 113 | Me | 6-NO$_2$ | — | EtOH | 204–5 |
| 114 | Me | — | 4-Et | EtOAc | 201–3 |
| 115 | Me | — | 4-CF$_3$ | EtOAc | 190–2 |

The $\alpha$-(6-nitro-1,2-dihydro-2-oxo-quinol-4-yl)-propionic acid starting material for the above Example 113 was obtained as follows:

$\alpha$-(1,2-Dihydro-2-oxo-quinol-4-yl)propionic acid (15g.) was added in portions to stirred fuming nitric acid cooled to 5° C. The rate of addition was such that the reaction temperature remained between 5° and 10° C. After the addition was complete, the mixture was stirred at ambient temperature for 40 minutes and was then poured into water (1.2 l.). The resultant solid was separated by filtration, washed with water and dried in vacuo to give $\alpha$-(6-nitro-1,2-dihydro-2-oxo-quinol-4-yl)propionic acid as a white solid (90% yield), with m.p. 276°–278° C. (decomposition).

EXAMPLE 116

$\alpha$-(1-Benzyl-1,2-dihydro-6-nitro-2-oxo-quinol-4-yl)-propionic acid (352 mg.) was dissolved in a mixture of 2N sodium hydroxide solution (0.5ml.) and water (4.5 ml.). Palladium on charcoal catalyst (33% Pd) (0.2g.) was then added and the resulting mixture was hydrogenated with shaking, at atmospheric pressure and at 20° C. during 3 hours. The catalyst was separated by filtration of the mixture through kieselguhr and the filtrate was acidified to pH 4 using glacial acetic acid. The resultant precipitate was collected by filtration and recrystallised from ethyl acetate. There was thus obtained $\alpha$-(1-benzyl-1,2-dihydro-6-amino-2-oxo-quinol-4-yl)propionic acid in 50% yield, m.p. 140°–2° C. (decomposition).

EXAMPLE 117

A solution of a methyl $\alpha$-(1-benzyl-1,2-dihydro-2-oxo-quinol-4-yl)propionate (250mg.) in methanol (3ml.) was mixed with a solution containing an excess of 9 molar equivalents of hydroxylamine in methanol (3ml.) and the mixture was left at 20° C. for 18 hours. The mixture was then poured into water (5ml.) and neutral material (largely unreacted methyl ester) was removed by extraction with ethyl acetate (3 $\times$ 5ml.). The aqueous phase was separated and acidified to pH 1 by addition of hydrochloric acid. The resultant precipitate was recrystallised from ethanol to give N-[$\alpha$-(1-benzyl-1,2-dihydro-2-oxo-quinol-4-yl)propionyl]hydroxamic acid in 40% yield, m.p. 211°–3° C. (decomposition).

EXAMPLES 118–122

The following compounds of formula I (wherein R$^3$ is a hydroxy radical) were prepared in yields of 27–65%, in a similar manner to that used in Example 1, but from the appropriate starting materials:

| Example | A | R$^1$ | R$^2$ | Substituent on ring X | Ring Y | m.p. ° C. (decomposition) | Recrystallisation Solvent |
|---|---|---|---|---|---|---|---|
| 118 | CH$_2$CH$_2$ | H | H | — | Ph | 196–7 | MeOH |
| 119 | (direct bond) | H | H | 7-MeO | Ph | 205–7 | EtOH |

| Example | A | $R^1$ | $R^2$ | Substituent on ring X | Ring Y | m.p. °C. (decomposition) | Recrystallisation Solvent |
|---|---|---|---|---|---|---|---|
| | | | | -continued | | | |
| 120 | $CH_2$ | Me | H | 6-Me | 3,4-$Cl_2$—Ph | 261-2 | MeOH/D.M.F. (2:1 v/v) |
| 121 | $CH_2$ | Me | H | — | 3,4-$Me_2$—Ph | 204-5 | EtOH |
| 122 | $CH_2$ | Me | H | 6-Cl | 3,4-$Cl_2$—Ph | 229-231 | EtOH |

The 1-benzyl-1,2-dihydro-4-methyl-2-oxo-quinolines of formula III (wherein $R^2$ is hydrogen), required as starting materials for the above Examples, were obtained as described hereinbefore and had the following melting points:

| A | $R^1$ | Substituent on ring X | Substituent on phenyl ring Y | m.p. °C. |
|---|---|---|---|---|
| $CH_2CH_2$ | H | — | — | 127-8 |
| (direct bond) | H | 7-MeO | — | 122 |
| $CH_2$ | Me | 6-Me | 3,4-$Cl_2$ | 138-9 |
| $CH_2$ | Me | — | 3,4-$Me_2$ | 107-8 |
| $CH_2$ | Me | 6-Cl | 3,4-$Cl_2$ | 154-6 |

EXAMPLES 123-127

The following compounds of formula XVIII were obtained in a similar manner to that described in Example 57 but from methyl iodide and the appropriately substituted 1-benzyl-1,2-dihydro-4-methyl-2-oxoquinolines, in yields of 20-62%:

| Example | A | $R^2$ | Substituent on ring X | Substituent on ring Y | m.p. °C. (decomposition) | Recrystallisation solvent |
|---|---|---|---|---|---|---|
| 123 | $CH_2$ | Me | — | 2-Me | 248 | EtOH |
| 124 | $CH_2$ | Me | 7-Me | — | 207-8 | EtOH |
| 125 | $CH_2$ | Me | 7-Me | 4-Cl | 175-7 | EtOH |
| 126 | $CH_2CH_2$ | Me | 6-Me | — | 185 | EtOH |
| 127 | $CH_2$ | Me | 6,7-$Me_2$ | 3,4-$Cl_2$ | 201 | EtOH |

The corresponding, new substituted 1-benzyl-1,2-dihydro-4-methyl-2-oxo-quinolines of formula III (wherein $R^1$ and $R^2$ are hydrogens), used as starting materials in the above Examples were obtained as described hereinbefore and had the following melting points:

| A | Substituent on ring X | Substituent on phenyl ring Y | Recrystallisation Solvent | m.p. °C. |
|---|---|---|---|---|
| $CH_2$ | — | 2-Me | Ethanol | 172-4 |
| $CH_2$ | 7-Me | — | Cyclohexane | 152 |
| $CH_2$ | 7-Me | 4-Cl | " | 154 |
| $CH_2CH_2$ | 6-Me | — | " | 110-2 |

EXAMPLE 128

1-(4-Nitrobenzyl9-1,2-dihydro-2-oxoquinol-4-ylacetonitrile (0.5g.) was added to a solution of sodium hydroxide (0.2g.) in ethanol (50ml.) and the mixture was heated under reflux for 5 hours. The ethanol was evaporated under reduced pressure and the residue was treated with 2N hydrochloric acid (100ml.). The precipitate thus formed was separated off and recrystallised from ethanol to give 1-(4-nitrobenzyl)-1,2-dihydro-2-oxoquinol-4-ylacetic acid (0.42g.) m.p. 208°-210° C., (decomposition).

The starting material was obtained as follows:

Ethyl 1-(4-nitrobenzyl)-1,2-dihydro-2-oxoquinol-4-ylpyruvate (19g.; obtained by the method described for the starting material in Example 73) and hydroxylamine hydrochloride (13.6g.) were added to a mixture of pyridine (150ml.) and ethanol (150ml.). The resulting solution was heated under reflux for 3 hours and the solvents were then evaporated under reduced pressure. The residue was triturated with water (65ml.) and the solid filtered off. Trituration of this solid with ethanol (100ml.) and filtration gave ethyl 3-[1-(4-nitrobenzyl)-1,2-dihydro-2-oxoquinol-4-yl]-2-oximinopyruvate (18.7g.) m.p. 267° C. (decomposition) which was sufficiently pure for use in the next stage of the reaction.

Ethyl 3-[1-(4-nitrobenzyl)-1,2-dihydro-2-oxoquinol-4-yl]2-oximino-pyruvate (8.7g.) was dissolved in a solution of sodium hydroxide (2.6g.) in aqueous methanol [100ml., MeOH:$H_2O$(2:1 v/v)] and the mixture was heated under relux for 1.5 hours. The cooled solution was acidified to pH3 with glacial acetic acid. The precipitate was filtered off, washed with water and dried in vacuo over phosphorus pentoxide. This dried solid (5.8g.) was suspended in acetic anhydride (50ml.) and the mixture was heated on a steam bath until gas evolution ceased and all the solid had dissolved. The solution was cooled to 0° C. and the solid was separated by filtration. A further crop of product was obtained by evaporating the filtrate to dryness and triturating the residue with ethanol. The combined solids were recrystallised from methanol to give 1-(4-nitrobenzyl)-1,2-dihydro-2-oxoquinol-4-ylacetonitrile (2.9g.) m.p. 190-93.

EXAMPLE 129

In a similar manner to that described in Example 88 there was obtained in 30% yield α-[6-methyl-1-(4-trifluoromethylbenzyl)-1,2-dihydro-2-oxoquinol-4-yl]propionic acid, m.p. 201°-3° C. (decomposition) (after recrystallisation from ethyl acetate), from α-(6-methyl-1,2-dihydro-2-oxoquinol-4-yl)propionic acid, m.p. 197° C. (decomposition), which was itself obtained in a similar manner to that described for the starting material in Example 88, but starting from 4,6-dimethyl-1,2-dihydro-2-oxoquinolone.

EXAMPLE 130

1-(3,4-Dichlorobenzyl)-3-methyl-1,2-dihydro-2-oxoquinol-4-ylacetic acid (200g.) is throughly mixed with lactose (400g.) and 10% w/v gelatin solution (9g.). The mixture is granulated and the granules are mixed with maize starch (35g.) followed by magnesium stearate (6g.). The mixture is then compressed into tablets containing 50, 100 or 250mg. of active ingredient.

The 1-(3,4-dichlorobenzyl)-3-methyl-1,2-dihydro-2-oxoquinol-4-ylacetic acid active ingredient may be replaced by a salt thereof or any one of the compounds of formula I described in any of the Examples 1 – 129.

What we claim is:

1. A compound selected from the group consisting of α-[1(4-ethylbenzyl)-1,2-dihydro-2-oxoquinol-4-yl]propionic acid, α-[1-(4-trifluoromethylbenzyl)-1,2-dihydro-2-oxoquinol-4-yl]propionic acid, α-(1-benzyl-7-methyl-1,2-dihydro-2-oxoquinol-4-yl)propionic acid, α-(1-benzyl-6-methyl-1,2-dihydro-2-oxoquinol-4-yl)propionic acid, α-[1-(-4-trifluoromethylbenzyl)-6-methyl-1,2-dihydro-2-oxoquinol-4-yl]propionic acid, α-[1-(4-chlorobenzyl)-6-methyl-1,2-dihydro-2-oxoquinol-4-yl]propionic acid, α-(1-benzyl-1,2-dihydro-2-oxoquinol-4-yl)propionic acid, α-[1-(4-methylbenzyl)-1,2-dihydro-2-oxoquinol-4-yl]propionic acid, α[1-(4-methylbenzyl)-6-methyl-1,2-dihydro-2-oxoquinol-4-yl]-propionic acid, and the pharmaceutically acceptable base addition salts thereof.

2. A quinolone alkanoic acid derivative of the formula:

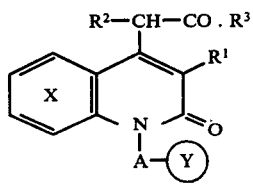

wherein A is a methylene, ethylene or propenylene radical; $R^1$ is hydrogen; $R^2$ is methyl; $R^3$ is hydroxy, amino, hydroxylamino, $C_{1-6}$ alkoxy or phenoxy; and wherein the benzene ring X is unsubstituted or bears either a single substituent selected from the group consisting of halogen atoms, methyl, methoxy, nitro and amino or two methyl substituents; and wherein the ring Y is phenyl which may optionally bear a single substituent selected from the group consisting of halogen, methyl, methoxy, methylthio and trifluoromethyl; or a pharmaceutically-acceptable salt thereof.

3. A compound as claimed in claim 2 wherein $R^3$ is a hydroxy radical.

4. A compound as claimed in claim 2 which is in an optically active form.

5. A compound as claimed in claim 2 selected from the group consisting of α-(1-benzyl-1,2-dihydro2-oxoquinol-4-yl)propionic acid and the pharmaceutically acceptable base addition salts thereof.

* * * * *